United States Patent
Gebhardt

(10) Patent No.: US 7,781,582 B2
(45) Date of Patent: Aug. 24, 2010

(54) PROCESS FOR THE PREPARATION OF 2-AMINO-[1,2,4]TRIAZOLO[1,5-A] PYRIMIDINES

(75) Inventor: Joachim Gebhardt, Wachenheim (DE)

(73) Assignee: Dow AgroSciences LLC, Indianapolis, IN (US)

( * ) Notice: Subject to any disclaimer, the term of this patent is extended or adjusted under 35 U.S.C. 154(b) by 806 days.

(21) Appl. No.: 10/584,720

(22) PCT Filed: Dec. 22, 2004

(86) PCT No.: PCT/EP2004/014596

§ 371 (c)(1),
(2), (4) Date: Apr. 9, 2007

(87) PCT Pub. No.: WO2005/063753

PCT Pub. Date: Jul. 14, 2005

(65) Prior Publication Data

US 2007/0238873 A1    Oct. 11, 2007

(30) Foreign Application Priority Data

Dec. 23, 2003   (EP) .................................. 03029728

(51) Int. Cl.
  *C07D 487/04*   (2006.01)
  *A01N 43/54*   (2006.01)
(52) U.S. Cl. ....................................... 544/263; 504/241
(58) Field of Classification Search ................. 544/263
  See application file for complete search history.

(56) References Cited

U.S. PATENT DOCUMENTS

| | | |
|---|---|---|
| 5,571,775 A | 11/1996 | Van Heertum et al. |
| 5,965,490 A | 10/1999 | Johnson et al. |
| 2002/0111361 A1 * | 8/2002 | Johnson et al. ........ 514/259.31 |

FOREIGN PATENT DOCUMENTS

| | | |
|---|---|---|
| WO | WO96/01826 | 1/1996 |
| WO | WO02/36595 | 5/2002 |

* cited by examiner

*Primary Examiner*—James O Wilson
*Assistant Examiner*—Susanna Moore
(74) *Attorney, Agent, or Firm*—Craig E. Mixan

(57) ABSTRACT

Process for the preparation of unsubstituted or substituted 2-amino-[1,2,4]triazolopyrimidines which comprises combining A) 2-amino-pyrimidine or its derivatives with alkyloxycarbonyl isothiocyanate or aryloxycarbonyl isothiocyanate with B) hydroxyl ammonium salt and a base wherein the reaction is carried out in a polar aprotic organic solvent in the temperature range of from 40 to 150° C.

6 Claims, No Drawings

PROCESS FOR THE PREPARATION OF 2-AMINO-[1,2,4]TRIAZOLO[1,5-A]PYRIMIDINES

Triazolopyrimidine derivates are valuable building blocks in pharmaceutical or agrochemical synthesis, e.g. fungicide, insecticide or herbicide synthesis.

WO 02/36595 A2 (Dow Agrosciences LLC) describes a synthesis route to 2-amino-5,7-dimethoxy[1,2,4]-triazolo[1,5-a]pyrimidine via reaction of 2-amino-4,6-dimethoxy pyrimidine plus ethoxycarbonylisothiocyanate.

The latter reaction is carried out at room temperature in tetrahydrofuran (THF) and the intermediate was isolated. This intermediate was than reacted with hydroxylaminehydrochloride and diisopropylamine in ethanol at room temperature yielding the 2-amino-5,7-dimethoxy[1,2,4]-triazolo[1,5-a]pyrimidine.

Yields of this two step process are not satisfying and the synthesis is not simple enough e.g. to be scaled up for commercial purposes.

The object of the present invention is to provide a simple process which leads to 2-amino-triazolopyrimidines in high yields, which in turn can be used as building blocks e.g. in agrochemical synthesis, such as fungicide, insecticide or herbicide synthesis.

Therefore the process as defined in the claims as well as the use of such process in the preparation of 2-amino[1,2,4]-triazole[1,5-a]pyrimidine structure containing agrochemicals or pharmacenticals has been found.

Stage A of the process of the instant invention is the combination of a substituted or unsubstituted 2-amino-pyrimidin and alkoxycarbonyl isothiocyanate or aryloxycarbonylisothiocyanate.

Prefered unsubstituted or substituted 2-amino-pyrimidines are such of formula I

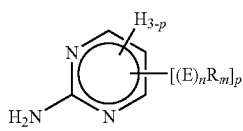

(I)

In which the variables have the following meaning.

E=independently the same or different are O, S, N, P;

R=independently the same or different are $C_{1-10}$-alkyl, $C_{6-20}$-aryl, $C_{7-20}$-arylalkyl, $C_{7-20}$-alkylaryl which each of those may be substituted with one or more of the following groups: F, Cl, Br, I, $C_{1-20}$-alkoxy, $C_{6-20}$-aryloxy, non substituted or preferably substituted amino; F, Cl, Br, I;

n=0 or 1 m=1 for E=O, S m=2 for E=N, P p=0, 1, 2 or 3

Preferred groups R are linear or branched $C_{1-6}$-alkyl such as methyl, ethyl, n-propyl, I-propyl, n-butyl, sec-butyl, i-butyl, t-butyl, neo-pentyl, n-pentyl, n-hexyl or $C_{7-20}$-arylalkyl such as benzyl or diphenylmethyl.

Preferred groups E are oxygen (O) or nitrogen (N).

Preferably E is 0, p is 1 or 2 and the ER-groups are positioned meta to each other.

Most preferably R is $C_{1-6}$-alkyl, E is 0, p is 2 and the ER-groups are postioned meta to each other.

Suitable compounds of formula I are 2-amino-pyrimidine; 2-amino-4,6-dimethoxy-pyrimidine; 2-amino-4,6-diethoxy-pyrimidine; 2-amino-4,6-di-n-propoxy pyrimidine; 2-amino-4,6-di-n-butoxy pyrimidine.

The alkoxycarbonyl or aryloxycarbonyl isothiocyanate of the present invention have preferably the following formula II:

(II)

In which R has the same meaning—including the preferable meanings—as for compounds of formula I.

Suitable compounds of formula II are methoxycarbonylisothiocyanate, ethoxycarbonylisothiocyanate.

Compounds of formula II are know in the literature and can be prepared by known methods e.g. by reaction of the respective organochloroformiates with alkalimetal (K, Na, Rb, Cs) or alkaline earth metal (e.g. Ca, Ba, Sr) thiocyanates in an organic solvent (see for example J. Heterocycl. Chem. 5, 837 (1968); J. Org. Chem. 55 (18), 5230-5231 (1990); U.S. Pat. Nos. 4,160,037; 4,778,921; 5,194,673). The organic solvent is preferably the one in which the reactions of the instant invention are conducted.

The foregoing combination yields a N-pyrimidin-2-yl-N'-carboalkoxy (or aryloxy)thiourea of the formula III

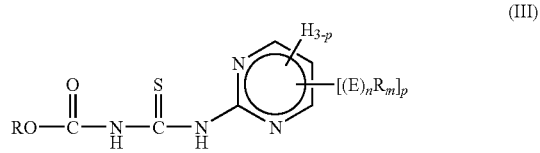

(III)

In which the variables have the same meaning—including the preferable meaning—as in formula I above.

Suitable compounds III are the ones with E=O, R=$C_{1-6}$-alkyl, m=1, p=1, 2 or 3, preferably are compounds III in which E=O, R=$C_{1-6}$-alkyl, m=1, p=2 in which the ER groups are positioned meta to each other. Very suitable compounds III are the following: N-(4,6-dimethoxypyrimidin-2yl)-N'-carboethoxythiourea, N-(4,6-diethoxypyrimidin-2yl)-N'-carboethoxythiourea.

Stage B of the instant invention is the combination of the compound III with a hydroxylammonium salt such as hydroxyl ammonium sulfate, hydroxyl ammonium chloride, hydroxyl ammonium nitrate, hydroxyl ammonium phosphate, preferably hydroxyl ammonium sulfate, in the presence of a base.

Preferable bases are alkali metal hydroxides (e.g. KOH, NaOH, RbOH, CsOH), earth alkali metal hydroxides (e.g. Mg(OH)$_2$, Ca(OH)$_2$, Ba(OH)$_2$, Sr(OH)$_2$) and organic bases like amines—preferably tertiary amines—pyridines and other herterocyclic organic bases, preferably cyclic amine bases. Most preferable bases are alkali hydroxides, in particular caustic soda (NaOH).

Preferably the base, e.g. caustic soda, is initially slowly added to establish a pH value of the reaction mixture of from 1 to 7.5 which is then maintained at pH 5 to 7.5, in particular pH 6.5 to 7.0 until the reaction is completed.

The above reaction sequence yields finally the respective 2-amino-[1,2,4]triazolopyrimidine IV

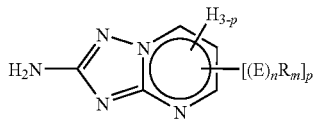
(IV)

In which the variables, including their preferable meaning, have the same meaning as under formula I.

Suitable compounds IV are the ones in which E=O, R=$C_{1-6}$-alkyl, m=1, p=1, 2 or 3 Preferable are compounds IV in which E=O, R=$C_{1-6}$-alkyl, m=1, p=2 in which the ER-groups are positioned meta to each other or in other words which occupy the 5-and 7-position (according to Chemical Abstract Nomenclature) of the triazolo pyrimidine ring system in formula (IV).

Very suitable compounds IV are: 2-amino-5,7-dimethoxy[1,2,4]triazolopyrimidine, 2-amino-5,7-diethoxy[1,2,4]triazolopyrimidine, 2-amino-5,7-di n or di iso propoxy[1,2,4]triazolopyrimidine, 2-amino-5,7-di n- or di tert. or di iso butoxy[1,2,4]triazolopyrimidine, in particular 2-amino-5,7-dimethoxy[1,2,4]triazolopyrimidine.

Usually stages A and B are conducted in polar aprotic solvents such as nitriles (e.g.aceto nitrile), ethers (e.g. thf, dimethoxyethane, dimethoxymethane, diethoxymethane, diisopropylether, 1,4-dioxan, methyltertbutylether (MTBE)), ketons (e.g. acetone, diethylketone, methylisobutylketone) or preferably in carboxylic acid esters, such as $C_{1-20}$-carboxylic-acid-$C_{1-10}$-alkylesters or the respective $C_{7-20}$-alkylarylesters or $C_{7-20}$-arylalkylesters.

Preferably $C_{1-20}$ carboxylic acid $C_{1-10}$-alkylesters are used as solvents.

Mixtures of the above-mentioned solvents are also suitable.

Most preferably the solvent in stage A is the same as the solvent in stage B.

Very most preferably the solvent in stage A and/or in stage B is a carboxylic acid ester, such as $C_{1-20}$-carboxylic-acid $C_{1-10}$-alkylester, preferably $C_{1-6}$-carboxylic-acid $C_{1-6}$-alkylester in which the carboxylic acid is a straight chain aliphatic carboxylic acid or a benzoic acid and the alcohol alkyl moiety is a straight chain alkyl; suitable examples for the carboxylic acid esters are methylacetate, ethylacetate, n-propylacetate, i-propylacetate, n-butylacetate, in particular ethylacetate.

Preferably reactions in stage A and/or stage B are conducted at temperatures of from 40 to 150° C., preferably 60 to 100° C., most preferably 70 to 90° C.

Very most preferably reactions of stage A as well as stage B are conducted under reflux of the respective solvent e.g. from 60 to 100° C., preferably 70 to 90° C.

Sometimes it might be necessary to conduct the reaction under pressure in order to achieve the abovementioned reaction temperatures.

Preferably no intermediates are isolated in the process of the instant invention ("one pot procedure"), although this isolation is easily possible by generally known methods.

The overall reaction time of stages A and B is usually of from 2 to 14 hours, preferably 5 to 6 hours.

The reaction products IV are in general worked up and isolated with the usual organic techniques.

The process of the instant invention can be used in the synthesis of agrochemicals or pharmacenticals e.g. agrochemicals as described in WO 02/36595 A2 (DOW Agrosciences LLC) or U.S. Pat. No. 5,571,775 (DOW Elanco) which are expressly incorporated by reference herein.

For example compounds IV, obtained by the process of the instant invention can be reacted with aryl—or heteroarylsulfonyl halogenides Ar-$SO_2$-Hal or (Hetaryl)-$SO_2$-Hal yielding respectice N([1,2,4]triazolo[1,5-a]pyrimidin-2-yl) aryl or heteroaryl sulfonamide compounds V, as described in WO 02/36595 A2 (DOW Agrosciences LLC)

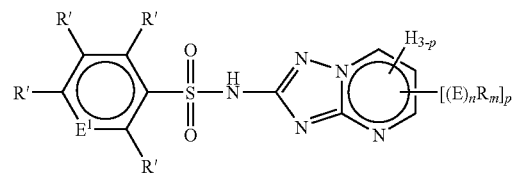
(V)

in which the variables have the same meaning as in formula I and R' independently the same or different is H or R and $E^1$ is CR' or N, preferably N.

Suitable compounds V are for example:

3-Pyridinesulfonamide, N-(5,7-dimethoxy[1,2,4]triazolo[1,5-a]pyrimidin-2-yl)-2-methoxy-4-(trifluoromethyl), as disclosed in Research Disclosure July 2002, 1230-1231;

3-Pyridinesulfonamide, N-(5,7-diethoxy[1,2,4]triazolo[1,5-a]pyrimidin-2-yl)-2-methoxy (trifluoromethyl).

The process of the instant invention leads in a simple, usually one pot procedure, to the valuable compounds IV in high yield, usually overall yield above 85%, in particular over 90%.

EXAMPLES

One pot procedure for the synthesis of 2-amino-5,7-dimethoxy[1,2,4]triazolopyrimidine (ADTP) from 2-amino-4,6-dimethoxypyrimidine (ADP)

11.9 g (0.075 mol) ADP was dissolved in 68 g ethyl acetate. 11 g (0.0825 mol) ethoxycarbonyl isothiocyanate was added within 20 min. at 78° C. (no exotherm). The mixture was stirred over 5 h at reflux (78-79° C.). 49.2 g (0.075 mol) hydroxylammonium sulfate (25% solution in water) were added and the mixture heated to 71° C. (reflux aceotrope). 50 g (0.1 mol) diluted caustic soda (2 mol/l) was added within 1 h to establish the pH from 1.3 to 6.5 and hold at 6.5-7.0 (offgas $CO_2$ and $H_2S$, slightly exotherm). The mixture was stirred over 6 h under reflux (71° C.) for reaction completion. The mixture was cooled down over night to 20° C. The product (ADTP) was filtrated and washed 3 times with each 25 g water to remove the salt (Na content after first wash 0.42%, after second 0.20%, after third 0.025%). Finally the solid ADTP was dried. Yield: 91.1% in respect to ADP, purity 95.3% (quantitative HPLC assay).

The invention claimed is:

1. A process for the preparation of unsubstituted or substituted 2-amino-[1,2,4]triazolopyrimidines which comprises combining A) a 2-amino-pyrimidine with an alkyloxycarbonyl isothiocyanate or an aryloxycarbonyl isothiocyanate and B) with a hydroxyl ammonium salt and a base wherein the reactions are carried out in a carboxylic acid ester solvent in the temperature range of from 40 to 150° C.

2. The process according to claim 1 wherein the pH value in step B) is increased over time and finally maintained in the range of from 5.5 to 7.5.

3. The process according to claim 1, wherein the hydroxylammonium salt is hydroxylammonium sulfate.

4. The process according to claim 1 wherein the 2-aminopyrimidine is described by formula I

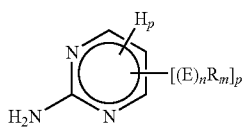

(I)

and the 2amino-[1,2,4]triazolopyrimidine is described by formula IV

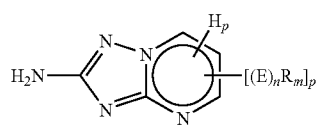

(IV)

wherein the variables have the following meaning:

E = independently the same or different are O, S, N, P;

R = independently the same or different are $C_{1-10}$-alkyl; $C_{6-20}$-aryl; $C_{7-20}$-arylalkyl; $C_{7-20}$-alkylaryl which each of those may be substituted with one or more of the following groups: F, Cl, Br, I, $C_{1-20}$-alkoxy, $C_{6-20}$-aryloxy, non substituted or preferably substituted amino; F, Cl, Br, I;

n = 0 or 1 m = 1 for E = O, S m = 2 for E = N, P p = 0, 1, 2 or 3.

5. The process according to claim 1, wherein the process is conducted without isolation of intermediates.

6. The process according to claim 1 wherein the 2-aminopyrimidine is 2-amino-4,6-dimethoxypyrimidine and the 2-amino-[1,2,4]triazolopyrimidine is 2-amino-5,7-dimethoxy [1,2,4]triazolo[1,5]-a]pyrimidine.

* * * * *